United States Patent [19]

Shoher et al.

[11] Patent Number: 4,990,394
[45] Date of Patent: Feb. 5, 1991

[54] METHOD AND MATERIALS FOR DENTAL STRUCTURES

[76] Inventors: Itzhak Shoher, 50 Shlomo-Hamelech St., Tel-Aviv, Israel, 64386; Aharon E. Whiteman, 13 J.L. Perez St., Petach-Tikvah, Israel, 49206

[21] Appl. No.: 348,942

[22] Filed: May 8, 1989

Related U.S. Application Data

[60] Continuation-in-part of Ser. No. 176,084, Apr. 1, 1988, abandoned, which is a division of Ser. No. 937,001, Dec. 2, 1986, Pat. No. 4,742,861.

[51] Int. Cl.$^5$ .................. B32B 7/02; B32B 5/18; A61C 8/00
[52] U.S. Cl. ..................................... 428/212; 428/44; 428/312.8; 428/328; 428/457; 428/550; 428/566; 428/613; 428/697; 428/913; 106/35; 419/2; 419/23; 419/65; 420/509; 433/201.1; 433/206; 433/228.1; 75/252
[58] Field of Search ............ 433/228.1, 201.1, 167, 433/171, 206, 207; 420/507–510; 419/2, 10, 23, 65; 75/208, 251, 252, 230, 255; 106/35; 164/92.1, 93, 95, 97, 98; 428/546, 547, 548, 550, 553, 613, 213, 304.4, 307.3, 148, 319.9, 158, 314.8, 212, 328, 357, 402, 457, 688, 689, 697, 539.5, 913, 512.2, 566, 560

[56] References Cited

U.S. PATENT DOCUMENTS

| | | | |
|---|---|---|---|
| 4,355,980 | 10/1982 | Dwight | 433/228 |
| 4,742,861 | 5/1988 | Shoher et al. | 164/80 |
| 4,814,008 | 3/1989 | Shoher et al. | 433/207 X |

*Primary Examiner*—Ellis P. Robinson
*Assistant Examiner*—Donald J. Loney

[57] ABSTRACT

The method and material of the present inventioin includes a combination of a high-fusing temperature metal component and a low-fusing temperature metal component which are adapted to be heat treated at a temperature above the melting temperature of the low-fusing temperature metal component, such that a porous, sponge-like structure is formed with a total void volume of 20–80%.

8 Claims, No Drawings

METHOD AND MATERIALS FOR DENTAL STRUCTURES

FIELD OF THE INVENTION

This application is a continuation-in part of U.S. Ser. No. 176,084 now abandoned which, in turn, is a division of U.S Application Ser. No. 937,001 now U.S. Pat. No. 4,742,861 issued May 10, 1988, and relates to a dental material and method for reinforcing a dental metal structure in forming, repairing or reinforcing a dental restoration.

BACKGROUND OF THE INVENTION

In crown and bridge prosthodontics, a wide diversification of retainers and pontics can be used in various combinations for constructing a bridge. A ceramic to metal restoration uses a framework of metal as reinforcement for the crown and bridge upon which is applied a fired-on coating of a ceramic material such as porcelain. The framework of metal may either be cast or formed from prefabricated units of preformed copings and pontics. In accordance with present practice, a framework may be altered by soldering, but otherwise cannot be modified or reinforced without involving investment and casting operations. Present practice is limited because of the unavailability of commercial materials with which to build up or extend the framework. To reinforce a framework without investment and casting requires adding material to the framework which upon heat treatment will become an integral part of the frame work. The material must be capable of being molded into a desired shape and must be self-supporting in the molded configuration as well as capable of retaining the shape in which it was molded under heat treatment. To be able to shape the material into a desired configuration, the material should be relatively soft and workable. Under heat treatment, the material should solidify into a rigid mass of metal without losing the shape in which it was molded prior to heat treatment. The material should fuse to the metal framework and should have a hardness characteristic of at least equal but preferably greater than the hardness of the material before heat treatment.

Such a material could be used, for example, to build up a cervical shoulder around a retaining member at the gingival margin without the need for investment or casting. For example, a finishing shoulder can be formed around a prefabricated metal coping which was preformed without a shoulder margin. The finishing shoulder can be molded into any shape by the dental technician. Likewise, the material can be used to build metal cusps upon a metal coping before ceramic porcelain is added to provide buccal and/or lingual cusp reinforcement. The material may also be used to strengthen joints at predetermined locations in the framework or for general bridgework repair. The latter is, at present, relatively impossible. Heretofore, the dentist and dental technical were essentially limited to use of cast dental structures and to materials useful as solders or fluxes. Neither the conventional solder nor flux is capable of being molded into a self-supporting configuration nor is either material capable of retaining a shape under heat treatment. Soldering alloys are, in fact, designed to melt and flow freely under the heat of a soldering flame and function to join metals by fusion. A flux is a non-oxidizing agent.

Although no dental material is presently commercially available for reinforcing a dental restoration, there have been attempts in the past to form such a material. All such attempts are based on using a composition which solidifies into a solid mass upon being heat treated and suffers from substantial shrinkage.

In Applicant's parent application, U.S. Ser. No. 176,084, of which this is a continuation-in-part, a dental material composed of metal particles is disclosed for forming, repairing or reinforcing a dental restoration. The composition of metal particles are loose granular particles, preferably held together with a binder, to form a paste or putty constituency which facilitates using the composition as a build up material for reinforcing the framework of a dental restoration. The material is intended to be applied to a metal retainer, shaped into a desired configuration and heat treated. A porous sponge-like structure is formed as a result of the heat treatment having the shape it was given prior to heat treatment. If desired, a low melting temperature filler material may be melted into the sponge-like structure to form an integral solid mass.

Under certain circumstances it is difficult, impractical or undesirable to build up the dental material into the final shape with exacting detail prior to heat treatment. This is due to the difficulty in carving the material to form curves and shapes having accurate contours with any detailed precision. Instead, it is preferable to modify or reshape the material after it is heat treated, either by grinding, pressing or burnishing. The porous structure formed heretofore was found to be vulnerable to breakage and/or to chipping or flaking during any post-cold working operation.

It has been discovered in accordance with the present invention that by the judicious selection of the particle composition of the components in forming the dental material, and the volume relationship between components based upon their specific gravities, a porous structure with a desired void volume may be formed which, upon heat treatment, can be readily reshaped with a minimal degree of susceptibility to breakage or chipping.

SUMMARY OF THE INVENTION

The dental material of the present invention is composed of a composition of metal particles adapted to be subjected to heat treatment at a predetermined heat treatment temperature for use in forming, repairing or reinforcing a dental restoration, comprising relatively large metal particles of a first high fusing temperature metal component having a melting point above said heat treatment temperature, and a second low fusing temperature metal component of smaller size particles adapted to substantially melt during said heat treatment for binding the particles of said high fusing temperature metal so as to form a porous sponge-like structure of said high fusing temperature metal particles interconnected by the melted low fusing metal component and with the second low fusing temperature metal component, being at least equal in percent by volume relative to the high fusing temperature metal first component in the porous sponge-like structure.

The method of the present invention comprises forming a dental material composition of metal particles composed of a high fusing temperature metal component and a low fusing temperature metal component, with said particles of said high fusing component being larger in size than said low fusing component, and selecting said low fusing component in a relationship by volume to said high fusing component based on their relative specific gravities, such that by heat treating said composition at a temperature above the melting temperature of said low fusing component, an open porous structure of metal is formed having a total void volume of between 20-80%, and cold working said porous structure into a desired predetermined shape for forming, reinforcing or repairing a dental restoration.

DESCRIPTION OF THE PREFERRED EMBODIMENTS

The dental material of the present invention is a composition of metal particles which can be molded and heat treated into a desired self-supporting shape for forming a dental reinforced structure or for repairing a dental restoration. The dental material is composed of a composition of metal particles containing a high fusing temperature, metal component of a single metal or a metal alloy, preferably of precious metals, and a low fusing temperature metal component. The low fusing temperature metal component should consist of a single metal or metal alloy in the form of particles or clad to the particles of the high fusing temperature, precious metal component. The melting temperature of the high fusing temperature metal component should be higher than the melting temperature of the low fusing temperature metal component, and higher than the temperature at which the material is heat treated. Under heat treatment, the low fusing temperature component melts to fuse the high temperature particles together at its point of contact to form a porous sponge-like structure which retains the shape it is given prior to heat treatment.

A binder or other suitable carrying vehicle may be added to the composition of metal particles in forming the dental material of the present invention to give the material a paste or putty-like constituency. This should make the material easier with which to work. A binder should be selected which will volatize during heat treatment without leaving a residue. Any suitable organic resinous or synthetic resinous material is acceptable such as, for example, ethylene or polyethylene glycol. In addition to a binder, a flux such as borax may be added to form the dental material of the present invention. The flux eliminates the formation of oxides.

The composition of metals forming the dental material should be bio-compatible for use in the mouth. Accordingly, precious metals and precious metal alloys are preferred although not essential. The precious metals may also be used in combination with non-precious metals. In the foregoing embodiments of the invention, the high fusing temperature metal composition is primarily composed of a combination of from 0 to 100% platinum and from 100 to 0% palladium, with or without other constituents such as gold. However, the high fusing component may be a single metal or a mixture of different particles of different metals. Gold may be added to the high fusing temperature metal composition to increase the affinity of the particles of the high fusing temperature component to the low fusing temperature component. The particles of the low fusing temperature metal is preferably composed of a gold alloy with gold as the major constituent or entirely of gold. The preference for gold as the major constituent of the low fusing component is based on its known characteristics of workability, non-oxidizing property and its color.

The size of the particle of the high fusing temperature metal component is an important characteristic of the present invention. Best results are achieved when the particle size of the high fusing temperature component is below about 100 microns and preferably below 74 microns. The high fusing temperature component particles should also be larger in size than the particle size of the low fusing component, and preferably about 2-10 times larger than the particle size of the low fusing component. The optimum size is about 5-10 times larger than the low fusing component. The low fusing component is preferably no larger than 50 microns in size, and optimally below 25 microns in size.

When the low fusing component is cladded to the particles of high fusing particles, the latter should also be much larger in size based upon relative thicknesses between the clad components. The shape of the particles of the high fusing component is considered important to the present invention, but is not a critical characteristic. Irregularly shaped particles in the form of flakes appear to function best. An irregular shape allows the particles to form a mesh or open interlocking network of particles. The low fusing metal component fuses the particles of the high fusing temperature at the contact points in the open network to form a porous sponge-like mass under heat treatment. Any shape is acceptable including a spherical shape, although strips and irregularly contoured shapes (particularly a crescent shape) is preferred.

Although the material of the present invention is a composition of metal particles, the method of forming the particles is not critical to the present invention and, as stated earlier, the low fusing component particles may be cladded to the high fusing component particles to form a composite of a high fusing temperature component and a low fusing temperature component. The cladded particles may have one component totally encapsulating the other or only partially covering one another. Cladded particles may be formed, for example, from multiple layered sheets which may have been laminated. Various other known deposition processes may also be used to form layered sheets or to encapsulate the particles one within the other including, for example, electrodeposition and cathode sputtering. Where the metal particles are cladded to one another, the proportion of the high fusing component to the low fusing component in the total composition would be based on the difference in the thickness between the cladded metals. Preferably the thickness of the low fusing component should be in a range of 8 to 15 microns for reasons which will be discussed hereafter.

The method of the present invention comprises forming a dental material composition of metal particles with a high fusing temperature component, as heretofore defined, in combination with a low fusing temperature component, as heretofore defined. The low fusing temperature component is intended to function primarily as a soldering agent for fusing the particles of the high fusing temperature metal together at their points of contact upon heat treatment. The concentration and volume percent of low fusing temperature metal particles will, however, control the void volume in the porous structure formed by heat treatment. A porous structure having a void volume of 20-80% is preferred with a void volume of 40-60% being optimal. Also, to develop a sponge-like structure which is easily shaped through cold working, such as by grinding, burnishing and/or pressing, the sponge particles have to be well fused together and relatively rigid. Accordingly, the volume of the low fusing component in the composition should be selected to produce a sponge having a desired void volume characteristic which will enable the porous structure to be reshaped. When the high fusing component is palladium or an alloy containing palladium in a range of from 35-100% palladium, the low fusing temperature component should represent 40-70% by volume of the heat treated porous structure, and preferably between 45-60% by volume of the porous structure. Optimally, the volume of the low fusing component in the porous structure should be at least approximately equal to, and preferably greater than the volume of the high fusing component. Moreover, the low fusing temperature metal component in the metal composition prior to heat treatment should also be, by weight percent, a range from about equal to, but preferably greater than the weight percent of the high fusing component in the composition. This generally results in a porous structure with a 40-60% void volume. The percent of metal by volume in the porous structure is derived from the weight percent of metal particles in the composition prior to heat treatment and by their specific gravities. The following six examples consisting of two groups, A and B of three different samples, are given for illustrative purposes.

| Sample | Percent by weight in composition before heat treatment | | Percent by volume in sponge after heat treatment | |
|---|---|---|---|---|
| | High fusing metal | Low fusing metal | High fusing metal | Low fusing metal |
| Group A | | | | |
| 1. | 33.76% | 66.24% | 45% | 55% |
| 2. | 53.63% | 46.37% | 65% | 35% |
| 3. | 21.07% | 78.93% | 30% | 70% |
| Group B | | | | |
| 1. | 47.26% | 52.74% | 45% | 55% |
| 2. | 67.36% | 32.64% | 66% | 35% |
| 3. | 32.26% | 67.74% | 30% | 70% |

In samples 1-3 of Group A, the high fusing component is palladium and the low fusing component is gold, whereas in Group B, the high fusing component is platinum and the low fusing component is gold. The particle sizes of the high fusing component vary between 10 to 70 microns for each Group A and B to provide the percent by weight indicated. The gold component is pure gold with particles of between 5 to 25 microns. The heat treatment temperature is 1100° C. The specific gravity for the palladium component is 12 gm/cm³ (grams per cubic centimeter) and the specific gravity for platinum is 21.45 gm/cm³. The different groups are based on the differences in specific gravity for the high fusing components and, as such, will affect the weight relationship before heat treatment.

The total void space for the product of samples 1 and 4 is 55%, for samples 2 and 5, it is 65%, and for samples 3 and 6, it is 35%.

Samples 1 and 4 form a sponge product which can be readily cold worked by either burnishing, pressing or grinding without breaking off particles or flaking. This is also true for samples 3 and 6, but they undergo substantial shrinkage during sintering. Samples 2 and 5 produce a sponge-like product which tends to break and flake under cold working applications, such as burnishing, grinding and pressing. Accordingly, the preferred materials provide a higher percent by volume of the low fusing component in the sponge, and a range of from nearly equal to a much greater percentage by weight of the low fusing component in the composition before heat treatment.

A binder and/or fluxing agent is added to the dental material composition before it is used as a build-up material. A binder may be added, as earlier explained, to give the dental material composition a paste-like clay consistuency which should make the material easier to work with. The dental material composition is applied to a dental structure, such as a metal coping or bridge, to add reinforcement to the structure at desired specific locations or to extend the structure, etc. The dental material may be applied to the structure by a brush or spatula and burnished or molded by hand into a desired shape. The dental structure, including the dental material, is then heat treated at a preselected heat treatment temperature by subjecting it to the flame of a Bunsen burner or by sintering in a furnace at a temperature below the melting temperature of the high fusing temperature component. The melting temperature of the high fusing temperature component should be above the selected heat treatment temperature which is usually a temperature below 1300° C. and preferably between about 1075° C. to 1175° C., although any desired temperature may be used as the heat treatment temperature provided it will melt the low fusing temperature metal component. Heat treatment causes the dental material composition to form a porous structure in the form of an open network of interconnected metal particles of generally sponge-like appearance which is fused to the dental structure. The porous sponge-like mass of metal retains the shape it was given prior to heat treatment with the degree of shrinkage during heat treatment related to the ratio of the low fusing temperature component to the high fusing temperature component. Although, in general, the lower the concentration of low fusing component, the lower the shrinkage, it does not necessarily follow that shrinkage is entirely undesirable and that therefore, in some cases, a higher ratio of low to high temperature component would be desirable. It may, for example, be desirable to control the amount of shrinkage in the metal sponge so as to tailor to the shrinkage to the anticipated shrinkage in the porcelain material when baked in the furnace during the fabrication of a porcelain to metal restoration. In the latter case, the volume percent of low fusing component in the sponge should be higher than the high fusing component. It may also be desirable to give the metal porous structure a "gold" look. This is preferably accomplished by using a low fusing component of gold or gold alloy with a substantially higher proportion of low fusing component relative to the high fusing component in the porous structure. A gold or gold alloy low fusing component is preferred for use with a palladium or palladium alloy high fusing component.

After heat treatment particles of filler having a low melting temperature are added to the porous mass of metal and heat treated to cause the filler particles to melt into the sponge-like porous mass for forming a solid reinforced structure. The particles of filler are preferably metal particles of gold. Heat treatment of the filler particles can be carried out at the same heat treatment temperature as originally carried out to form the porous mass. The low fusing temperature in the porous mass was melted during heat treatment to form an alloy with the high fusing metal at the points of contact where the low fusing component solidifies. The metal alloy has a higher melting temperature than the melting temperature of the original low fusing component and, accordingly, it will not remelt upon renewed heat treatment at the same temperature. Alternatively, filler particles can be selected with a different melting temperature than the original melting temperature of the low fusing metal component. For example, the filler particles can be gold and the low fusing metal a gold alloy, or they can both be pure gold o gold alloys. Other metals may also be used. Moreover, the porous sponge may be filled with filler particles of a ceramic composition such as porcelain, where strength is not required and particularly for repair of a chipped porcelain restoration.

The low fusing metal component may consist of a single metal such as pure gold or an alloy thereof or of more than one metal alloy in combination. When the low fusing component is plated onto the particles of the high fusing component to form cladded particles, it is important that the thickness of the low fusing component be small relative to the thickness of the high fusing component. The preferred thickness is between 8-15 microns. The high fusing metal component may be a composition of gold, platinum and palladium with minor additions of other constituent elements, with the combination of palladium and/or platinum being the major constituent.

It should be understood that the invention is not to be construed as limited to any given dental application for the material. The material may, for example, be added to a dental framework after the porcelain has been fired. If, for example, a crown is too short at the margin, this material may be used to extend the crown. Accordingly, the word "reinforce" is not to be given a narrow interpretation, but is instead to be given a much broader definition so that it specifically encompasses the idea of increasing the size and physical dimensions of the framework by simply adding to or extending the framework. In fact, the whole dental restoration—be it a crown, inlay or onlay—can be made with the dental material of the present invention. In the same manner, the material of the present invention may be used to fill a space between adjacent teeth upon which a fired-on ceramic veneer may be applied, if desired, or to form a coping for a dental restoration.

What is claimed is:

1. A dental material for forming, repairing or reinforcing a dental restoration comprising a composition of metal particles subjected to heat treatment at a preselected temperature level for carrying out the function of forming, repairing or reinforcing a dental restoration, said composition, including metal particles of a first high fusing temperature metal component having a melting point above the selected heat treatment temperature and metal particles of a second low fusing temperature metal component which substantially melts during said heat treatment, and being smaller in size than the high fusing metal particles, such that upon said heat treatment, a porous sponge structure is formed having a total void volume of between 20-80% with the concentration of the low fusing metal component in the porous sponge being substantially equal or greater than the high fusing metal component in percent by volume such that said porous sponge structure may be readily reshaped by grinding, burnishing and/or pressing.

2. A dental material, as defined in claim 1, wherein said porous sponge structure has a total void volume of about 40% to 60%.

3. A dental material, as defined in claim 2, wherein the volume percent of the low fusing component in said porous structure is greater than the volume percent of said high fusing metal component.

4. A dental material, as defined in claim 3, wherein said high fusing temperature metal component contains palladium in a range of from about 35% to 100%, and wherein said low fusing temperature metal component should represent 40% to 70% by volume of the heat treated porous structure.

5. A dental material, as defined in claim 4, wherein said low fusing temperature metal component is gold or a gold alloy.

6. A dental material, as defined in claim 3, wherein said high fusing temperature metal component is at least two times larger in size than the low fusing temperature metal component.

7. A dental material, as defined in claim 6, wherein said high fusing temperature metal particles are at least five times larger in size than the low fusing temperature metal particles.

8. A dental material, as defined in claim 5, wherein said composition of metal particles further comprises a binder to give the material a creamy consistency.

* * * * *